(12) United States Patent
Iggulden et al.

(10) Patent No.: US 6,612,182 B1
(45) Date of Patent: Sep. 2, 2003

(54) CONTAINER AND TESTING DEVICE FOR SPORT BALLS

(75) Inventors: Jerry Iggulden, 10345 W. Olympic Blvd., Los Angeles, CA (US) 90064; Peter D. Lippire, Goleta, CA (US)

(73) Assignee: Jerry Iggulden, Los Angeles, CA (US)

( * ) Notice: Subject to any disclaimer, the term of this patent is extended or adjusted under 35 U.S.C. 154(b) by 0 days.

(21) Appl. No.: 09/993,278

(22) Filed: Nov. 5, 2001

Related U.S. Application Data

(63) Continuation-in-part of application No. 09/574,549, filed on May 18, 2000, now Pat. No. 6,360,613.

(51) Int. Cl.[7] ............................................... G01N 3/08
(52) U.S. Cl. ..................................................... 73/820
(58) Field of Search ........................... 73/820, 824, 818

(56) References Cited

U.S. PATENT DOCUMENTS

| | | |
|---|---|---|
| 3,665,757 A | 5/1972 | Hoag |
| 3,987,699 A | 10/1976 | Popenoe |
| 4,136,554 A | 1/1979 | Larson |
| 4,154,095 A | 5/1979 | Snyder |
| 5,222,391 A | 6/1993 | Reenstra |
| 5,245,862 A | 9/1993 | Zeiss |
| 5,291,774 A | 3/1994 | Putnam, Jr. |
| 5,511,410 A | 4/1996 | Sherts |
| 5,567,870 A | 10/1996 | Harris |
| 5,603,165 A * | 2/1997 | Bernhardt et al. ............ 33/509 |
| 5,639,969 A | 6/1997 | D'Adamo |
| 5,760,312 A * | 6/1998 | MacKay et al. ................ 73/81 |
| 5,837,889 A * | 11/1998 | Slenker .......................... 73/81 |
| 6,360,613 B1 * | 3/2002 | Iggulden ....................... 73/820 |

FOREIGN PATENT DOCUMENTS

| | | |
|---|---|---|
| DE | 36 27 359 A | 2/1988 |
| GB | 230250 | 3/1925 |

* cited by examiner

*Primary Examiner*—Max Noori
(74) *Attorney, Agent, or Firm*—Blakely, Sokoloff, Taylor & Zafman

(57) ABSTRACT

A container for storing sport balls incorporates a device for testing the playing condition of the balls. The test device is in the form of a disk with a base portion supported within the container and an indicator arm. A ball to be tested is placed into the container where it rests on the indicator arm with a portion of the ball protruding out of the open end of the container. The exposed portion of the ball is pressed against a flat surface. This deflects the indicator arm and provides a visual indication of the playing condition of the ball.

11 Claims, 3 Drawing Sheets

CONTAINER AND TESTING DEVICE FOR SPORT BALLS

RELATED APPLICATION

This is a continuation-in-part of co-pending application Ser. No. 09/574,549 filed May 18, 2000 now U.S. Pat. No. 6,360,613.

FIELD OF THE INVENTION

This invention relates generally to the field of sport balls, such as tennis balls. More particularly, the invention comprises the combination of a container for a plurality of sport balls with a device for testing the playing condition of the balls.

BACKGROUND

Tennis balls and certain other types of sport balls, such as racquetballs and handballs, are manufactured with a predetermined internal pressure, which imparts resiliency. The pressure is retained within a sphere of elastomeric material; however, the material is not perfectly impermeable. The internal pressure diminishes over time and with extended play. As the pressure diminishes, so does the resiliency of the ball, which has a deleterious effect on the playing characteristics of the ball.

Official organizations for tennis and other sports have established specifications for the balls used to play the respective sports. For example, the International Tennis Federation (ITF) Rules of Tennis specify that the ball shall have a bound of more than 53 inches and less than 58 inches when dropped 100 inches upon a concrete base. The Rules also specify that the forward and return deformation of the ball when placed under a load of 18 pounds shall be between 0.220 inch and 0.290 inch. Both of these specifications relate to the resiliency of the ball and hence to its playing characteristics. Recreational players are generally not concerned with whether or not a particular ball meets the precise specifications of an official organization. Such players are more concerned with the general playability of a ball and will often test a ball by squeezing it by hand or bouncing it on pavement. These informal tests are highly subjective. A number of devices have been proposed for objectively testing sport balls, particularly tennis balls. Such devices are shown, for example, in U.S. Pat. Nos. 5,222,391; 5,245,862; 5,291,774; 5,511,410; 5,567,870; 5,639,969; and 5,760,312.

Some of the prior art testing devices shown in the above-mentioned patents are intended for laboratory use, while others are intended to be used by individual players. However, all of the known prior art devices are relatively complex and, therefore, relatively expensive. Many of the devices have electronic components and all have one or more moving parts. There remains a perceived need for an inexpensive ball tester that can be provided to consumers at the time that the balls are purchased, analogous to the way that many dry cell batteries are sold with integral devices for testing the condition of the battery. Preferably, such a device would be simple to use and would be incorporated into the package in which balls are sold and stored so that the player would not be burdened with the inconvenience and weight of an additional item to carry.

SUMMARY OF THE INVENTION

The present invention provides a device for testing the playing condition of sport balls. The invention is preferably configured as a testing device in combination with a container for storing the sport balls; however, the invention may also be configured as a stand-alone testing device. In one embodiment particularly suited for testing tennis balls, the invention comprises a generally cylindrical canister substantially similar to conventional tennis ball canisters. A ball condition test disk is inserted into the canister and supported by means on the inside wall of the canister. The disk has a base portion, which is supported within the canister, and an indicator arm. A ball is placed into the canister where it rests on the indicator arm with a portion of the ball protruding out of the open end of the canister. When the protruding portion of the ball is pressed against a flat surface, the indicator arm is deflected, thereby giving an indication of the playing condition of the ball.

DETAILED DESCRIPTION OF THE INVENTION

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of wellknown methods and devices are omitted so as to not obscure the description of the present invention with unnecessary detail.

Figure 1:
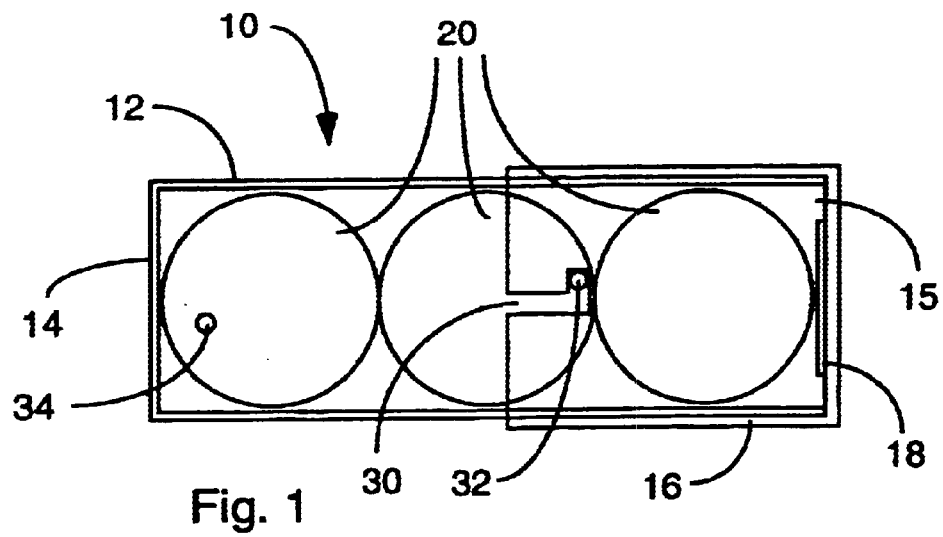
FIG. 1 is a side view of a first type of combination container and tester in accordance with the present invention.

FIG. 1 illustrates a combination ball container and tester 10 in accordance with the present invention. Container/tester 10 comprises a cylindrical tube 12 closed at end 14 and a cap 16. In the case of a device for tennis balls, cylindrical tube 12 is preferably dimensioned to house three or four balls 20 as is customary. Cylindrical tube 12 is preferably made of a clear plastic material, such as PETE, of sufficient strength to maintain internal pressurization sufficient for extended storage of balls 20 prior to use. A pressure seal (not shown) is provided at end 15 of tube 12 under cap 16. The pressure seal is removed and discarded by the consumer when balls 20 are first used.

Cap 16 preferably includes a plurality of L-shaped slots 30 which cooperate with protrusions 32 on cylindrical tube 12 to provide a bayonet-type fitting to retain cap 16 in place. Slots 30 may have a spiral configuration to provide a mechanical advantage when securing cap 16 in place. Alternatively, tube 12 and cap 16 may have cooperating screw threads instead of a bayonet-type fitting. Cap 16 allows container/tester 10 to be used for conveniently storing and transporting balls 20 even after the pressure seal has been removed from tube 12. Cap 16 is preferably made of a clear plastic material, but is preferably somewhat more rigid than tube 12. Thus, cap 16 may be made of styrene, polycarbonate or similar material.

Figure 2:
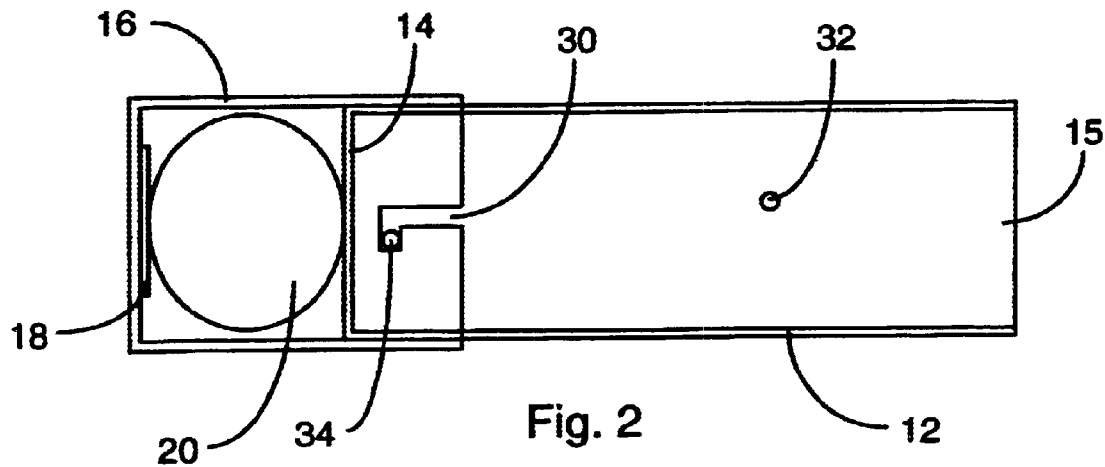
FIG. 2 is a side view of the apparatus of FIG. 1 in a ball-testing configuration.

Referring now to FIG. 2, a ball 20 is shown being tested for playing condition. The ball is placed inside cap 16 and the cap is secured over closed end 14 of tube 12 with slots 30 engaging protrusions 34. Protrusions 34 are spaced from end wall 14 so that ball 20 is slightly compressed when cap 16 is secured in place. As explained above, ITF specifications call for a forward deformation of more than 0.220 inch and less than 0.290 inch under a load of 18 pounds. Thus, if the dimensions are selected so that cap 16 compresses ball 20 by an amount in the specified range, a ball in new condition will exert a force of approximately 18 pounds against cap 16. In order to ascertain the playing condition of the ball, it is simply necessary to obtain an approximate measure of the force exerted against cap 16. Any suitable force indicator may be used, such as, for example, a spring-operated indicator or an electronic display coupled to a pressure transducer.

In one preferred embodiment, an indicator 18 is attached to the inside of cap 16. Indicator 18 comprises an opaque fluid enclosed within a pouch of flexible plastic. An indicator of this type is disclosed in U.S. Pat. No. 3,987,699, the disclosure of which is incorporated herein by reference. When the fluid within indicator 18 is displaced as a result of pressure exerted against indicator 18 by compressed ball 20, a visual indication of the displacement is provided. For example, the fluid may be a dark color, which in the absence of pressure completely obscures an underlying color on one wall of the pouch. When the thickness of the fluid is sufficiently reduced, the underlying color shows through. The degree to which the underlying color appears is directly related to the pressure exerted against indicator 18 and thereby provides a visual indication of the playing condition of ball 20.

Figure 3:
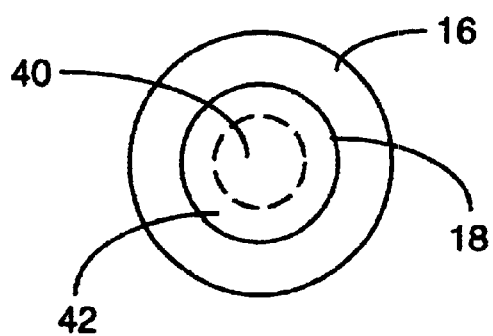
FIG. 3 is an end view of the testing device showing the ball condition indicator.

FIG. 3 is an end view of cap 16, through which indicator 18 may be viewed. A ball in good playing condition will exert sufficient force against indicator 18 to displace the fluid therein within a central region 40. Region 40 will thus have a different hue from surrounding region 42. A ball in poorer playing condition will exert less force against indicator 18 and the color differentiation between regions 40 and 42 will be diminished. In addition, the diameter of central region 40 will appear reduced. A ball in very poor condition will exert insufficient force against indicator 18 to displace the fluid and the entire face of indicator 18 will appear as a solid hue.

Figure 4:
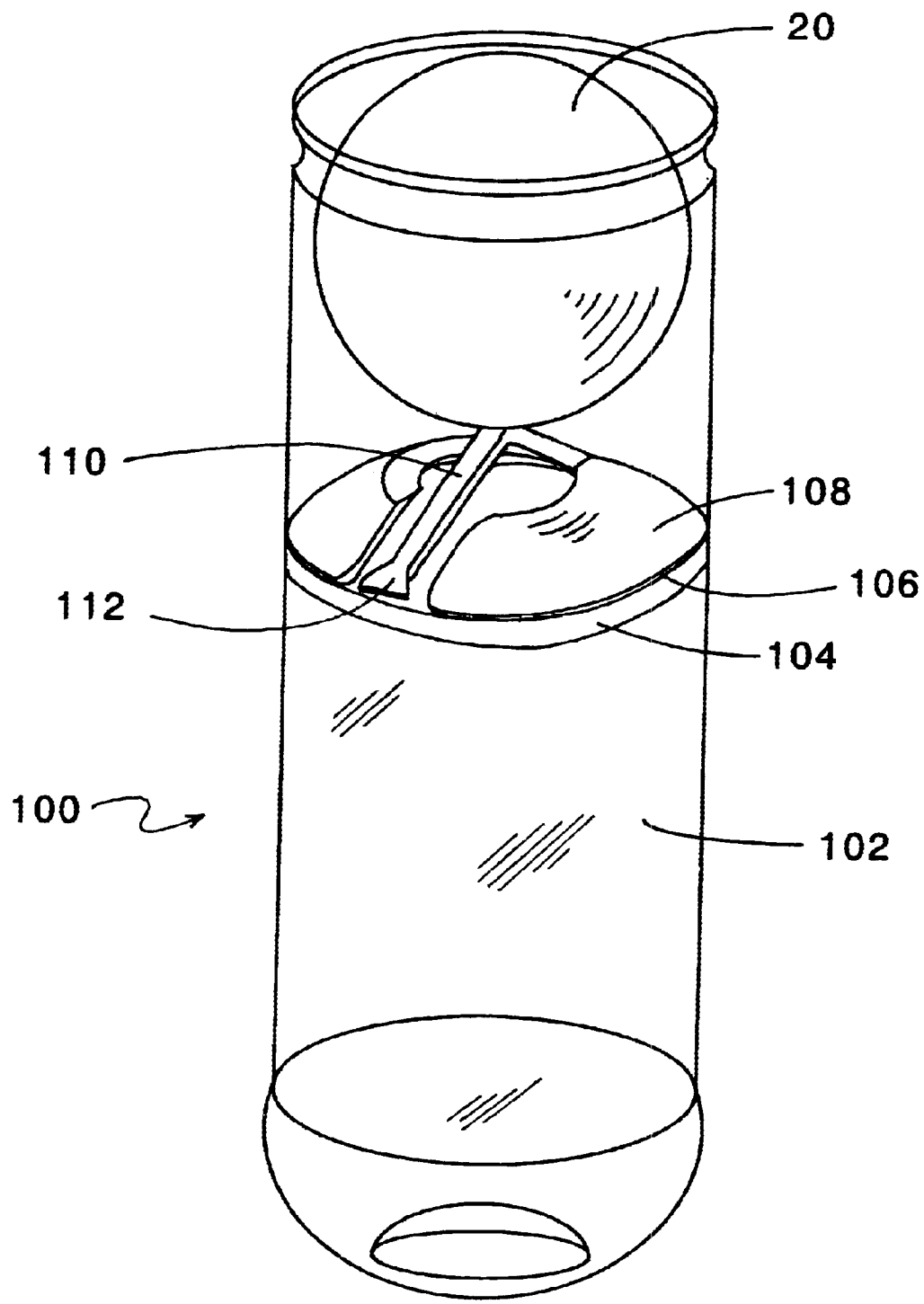
FIG. 4 is a perspective view of a second type of combination container and tester in accordance with the present invention.

FIG. 4 illustrates an alternative embodiment of the invention 100. A can or canister 102 for storing a plurality, typically three, tennis balls is substantially similar to conventional tennis ball canisters. Canister 102 is preferably made of a clear plastic material, such as PETE. Canister 102 differs from a conventional tennis ball canister in that it is provided with means 104 for supporting a ball-testing disk 106. As illustrated, supporting means 104 may comprise a circumferential rib on the interior surface of canister 102. Alternative support means may also be employed, for example, disk 106 may be supported by a plurality of dimples or similar protrusions on the inner surface of canister 102. Whichever means of support are employed, it is important that they protrude into the interior volume of canister 102 only enough to adequately support disk 106, but not so much as to interfere with the movement of balls 20 throughout the volume.

Figure 5:
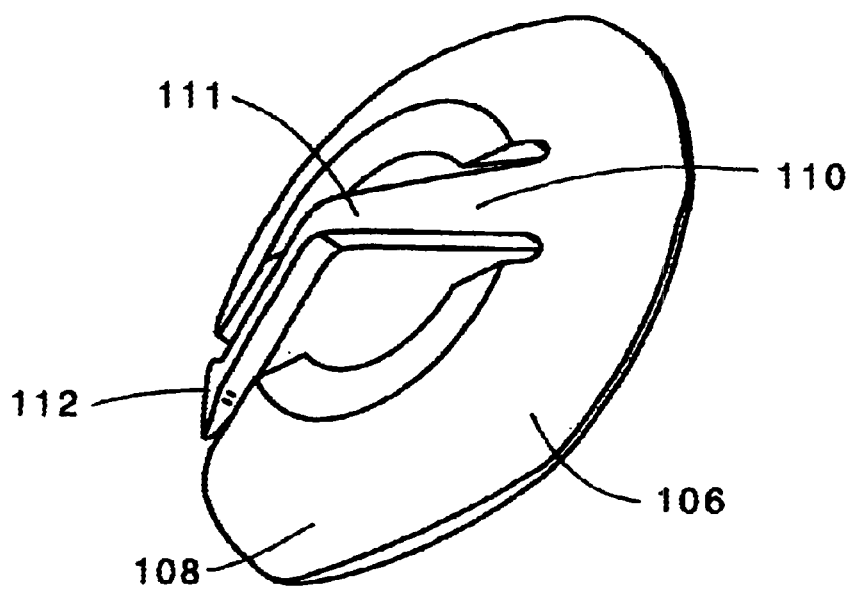
FIG. 5 is a detailed view of the ball condition tester seen in FIG. 4.

Referring to FIG. 5, ball-testing disk 106 has a generally conical shape defined by skirt portion 108. The outer diameter of disk 106 is such that it may be easily inserted into canister 102, but will be firmly supported by support means 104. Disk 106 includes an indicator arm 110 with an indicator tip 112. The indicator arm 110 has as inverted "V" shape with a relatively sharp point 111. This provides for a small area of contact between the indicator arm and the ball being tested, thereby maximizing the deflection of the indicator arm.

Disk 106 is preferably made of a relatively rigid plastic material, such as Delrin or the like. The disk is preferably made by an injection molding process and may be engraved with a product logo, etc. Due to the generally conical shape of the disk, a plurality of the disks will naturally tend to nest and can be easily stacked in a shipping container or a dispenser for placing the disks into tennis ball canisters.

Figure 6:
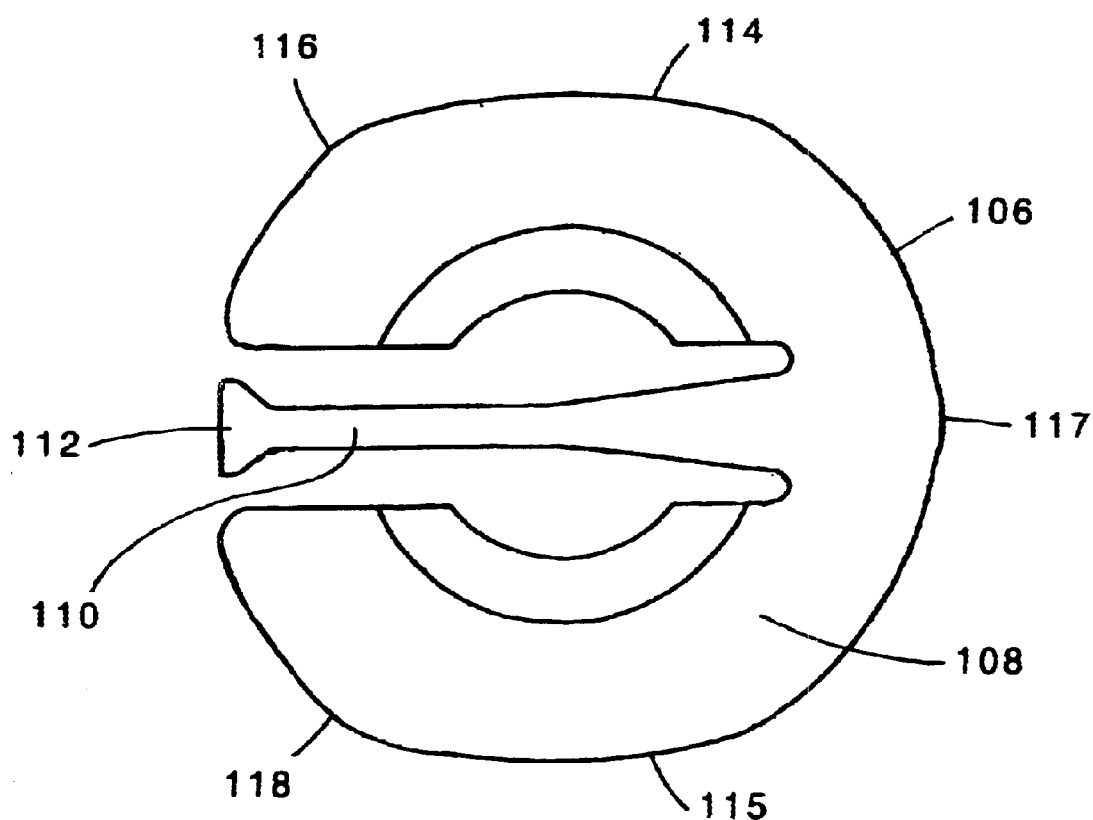
FIG. 6 is a top plan view of the ball condition tester.

FIG. 6 is a top plan view of ball-testing disk 106. While the disk has a generally circular outer perimeter corresponding to the circular cross-section of canister 102, it can be seen that the sides 114, 115 of disk 106 are somewhat flattened. This facilitates the insertion of disk 106 through the opening of canister 102. The outer perimeter of disk 106 bulges outwardly slightly at 116, 117 and 118 to ensure that the disk will be securely supported by support means 104. These bulges also hold disk 106 in place when canister 102 is inverted. It should be noted that indicator tip 112 is set back slightly from the outer perimeter of the disk to ensure that it will not strike the support means 104 when indicator arm 110 is deflected during a test of ball condition.

Referring again to FIG. 4, the playing condition of a ball 20 is tested by first placing disk 106 on support means 104 and then inserting ball 20 into canister 102 to rest upon indicator arm 110. A portion of ball 20 protrudes from the opening of canister 102. The canister is grasped and the protruding portion of ball 20 is placed against a flat surface, such as a wall or tabletop. Pressure is applied on the canister until the rim of the opening contacts the flat surface. The pressure causes the indicator arm 110 to be deflected. The amount of deflection is a function of the rigidity of ball 20. This, in turn, is a function of the internal pressure in ball 20. A fresh ball, having an internal pressure established at the time of manufacture, will provide the greatest deflection of indicator arm 110. Over the life span of the ball, the pressure decreases and the amount of deflection is correspondingly less. At some point, the pressure decreases to an extent that the ball is no longer considered playable. The playing condition of ball 20 is thus ascertained by the deflection of indicator arm 110 as seen by the position of indicator tip 112 viewed through the transparent wall of canister 102. The wall of canister 102 may be provided with a scale or other indicia by which the deflection of indicator arm 110 may be measured. The scale may provide a quantitative measure of ball condition or may simply provide a pass/fail indication. In one embodiment, canister 102 may be provided with a frosted ring or band surrounding support means 104. The frosted band may extend down the side of canister 102 far enough to obscure indicator tip 112 in all positions except when deflected by a ball in playable condition. Thus, when a ball is tested, the appearance of indicator tip 112 below the frosted band provides an indication that the ball is in playable condition.

An individual ball 20 may be easily tested for playing condition as described above. The invention also facilitates rapid testing of a plurality of balls, such as may be required, for example, by a pro shop. This is easily accomplished by placing the balls to be tested on a flat surface, such as a tabletop. Canister 102, with ball-testing disk 106 installed, is then simply pressed down on each of the balls in succession. The playing condition of the ball is observed with indicator tip 112 and the ball may then be kept or discarded in accordance with its indicated playing condition. Pressure on the canister may be released to roll the ball around on the supporting surface to bring the point 111 of disk 106 into contact with the ball at multiple locations on the surface of the ball. Thus, a ball may be tested at the multiple locations to determine an "average" playing condition. This also allows the ball to be tested at an optimum location, such as on a seam. Optionally, the sport balls may be provided with a marking, either at the time of manufacture or subsequently, to indicate a test location so as to enhance repeatability of the test.

It will be recognized that the above-described invention may be embodied in other specific forms without departing from the spirit or essential characteristics of the disclosure. Thus, it is understood that the invention is not to be limited by the foregoing illustrative details, but rather is to be defined by the appended claims.

What is claimed is:

1. A device for testing a playing condition of a sport ball comprising:

a container having an interior volume to accommodate at least two sport balls;

means for partitioning the interior volume to create a test chamber open at one end of the container, the test chamber sized to accommodate a single sport ball with a portion thereof protruding from the end of the container, wherein the means for partitioning comprises a disk inserted into the container; and an indicator providing a visible indication of playing condition when said single sport ball is placed within the test chamber and the end of the container is pressed against a surface.

2. The device of claim 1, wherein the container includes a support for the disk on an interior wall.

3. The device of claim 2, wherein the support for the disk is molded into the interior wall.

4. The device of claim 3, wherein the support for the disk comprises a circumferential rib protruding from the interior wall.

5. The device of claim 3, wherein the support for the disk comprises a plurality of protrusions on the interior wall.

6. The device of claim 1, wherein the indicator is formed integrally with the disk.

7. The device of claim 6, wherein the indicator comprises an arm attached to the disk.

8. The device of claim 7, wherein the indicator comprises an arm with an inverted "V" shape, a first leg of which is attached to the disk and a second leg of which comprises a deflection indicator.

9. The device of claim 1, wherein the container is transparent.

10. The device of claim 9, wherein the visible indication of playing condition is provided by a position of the indicator viewed from outside the container.

11. The device of claim 10, wherein the container includes indicia of playing condition disposed in proximity to the position of the indicator.

\* \* \* \* \*